United States Patent
Hazel et al.

(10) Patent No.: US 9,527,063 B2
(45) Date of Patent: Dec. 27, 2016

(54) PROCESS FOR TREATING ZEOLITE CATALYSTS

(71) Applicant: BP CHEMICALS LIMITED, Middlesex (GB)

(72) Inventors: Nicholas John Hazel, East Yorkshire (GB); David Linke, Rostock (DE)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 14/761,484

(22) PCT Filed: Jan. 17, 2014

(86) PCT No.: PCT/EP2014/050881
§ 371 (c)(1),
(2) Date: Jul. 16, 2015

(87) PCT Pub. No.: WO2014/111508
PCT Pub. Date: Jul. 24, 2014

(65) Prior Publication Data
US 2015/0360211 A1    Dec. 17, 2015

(30) Foreign Application Priority Data

Jan. 21, 2013  (EP) .................................... 13152102

(51) Int. Cl.
*B01J 29/18*   (2006.01)
*C07C 51/09*   (2006.01)
*C07C 67/37*   (2006.01)

(52) U.S. Cl.
CPC ................ *B01J 29/18* (2013.01); *C07C 51/09* (2013.01); *C07C 67/37* (2013.01); *B01J 2229/36* (2013.01)

(58) Field of Classification Search
CPC ........ B01J 29/18; B01J 2229/36; C07C 51/09; C07C 67/37
See application file for complete search history.

(56) References Cited

U.S. PATENT DOCUMENTS 7,465,822 B2   12/2008  Cheung et al.
2006/0252633 A1   11/2006  Ghosh et al.

FOREIGN PATENT DOCUMENTS

| EP | 0 119 023 A2 | 9/1984 |
| WO | WO 94/15875 A1 | 7/1994 |
| WO | WO 2006/121778 A1 | 11/2006 |
| WO | WO 2009/077739 A1 | 6/2009 |
| WO | WO 2009/077745 A1 | 6/2009 |

OTHER PUBLICATIONS

Cheung et al., "Selective Carbonylation of Dimethyl Ether to Methyl Acetate Catalyzed by Acidic Zeolites," Angew. Chem. Int. Ed., 2006, 45, 1617-1620.*
Database WPI, Week 199430, Thomson Scientific, AN 1994-249069, 1 pg. (XP-002698178).

* cited by examiner

*Primary Examiner* — Paul A Zucker
*Assistant Examiner* — Mark Luderer
(74) *Attorney, Agent, or Firm* — Nixon & Vanderhye P.C.

(57) ABSTRACT

Process for treating a zeolite catalyst for the carbonylation of dimethyl ether to produce methyl acetate, in which the catalyst is contacted with a treatment gas containing water vapor in an amount of at least 1 mol % and at a temperature below which dealumination of the zeolite structure occurs. The zeolite contains at least one channel which is defined by an 8-member ring and is mordenite.

25 Claims, 2 Drawing Sheets

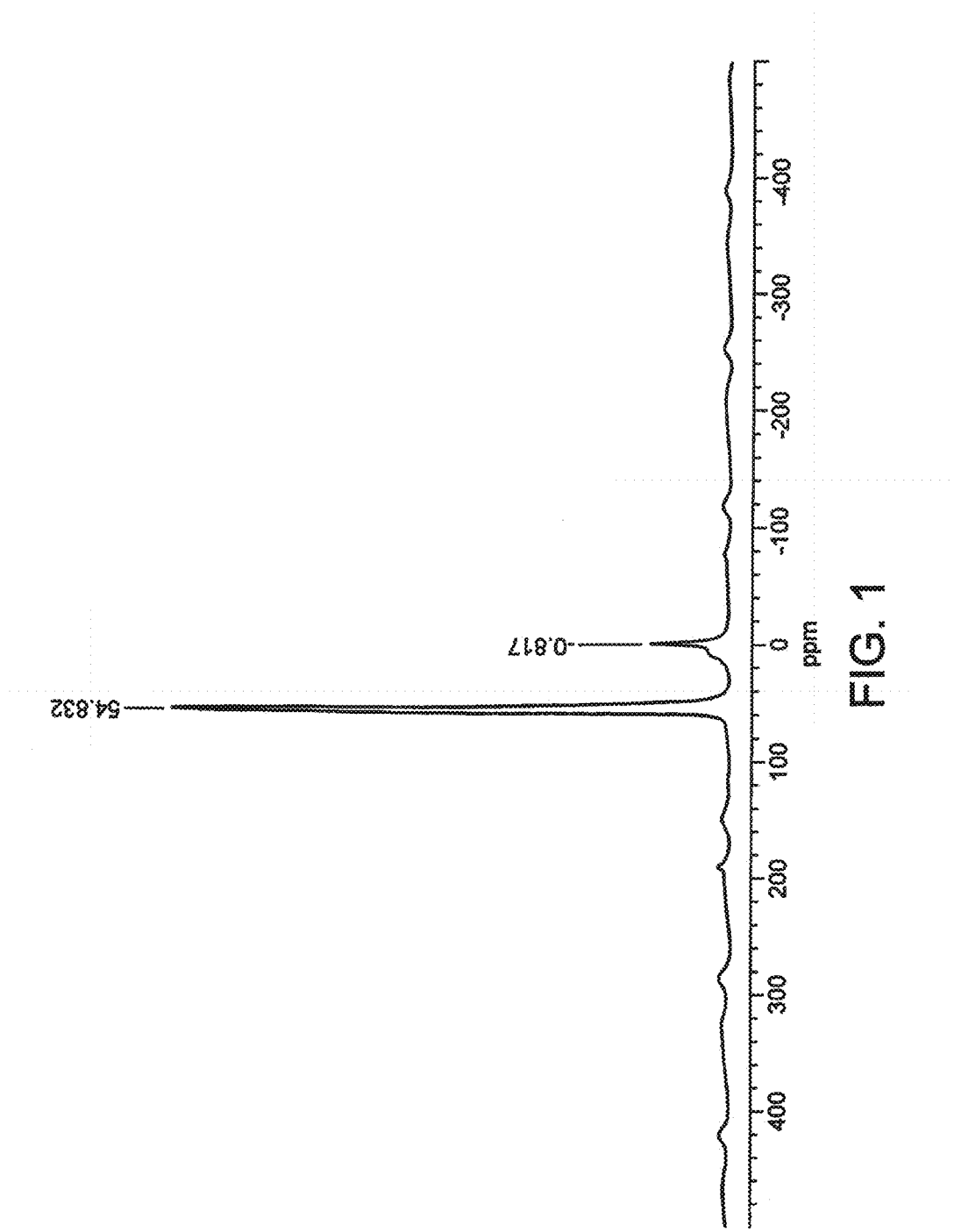

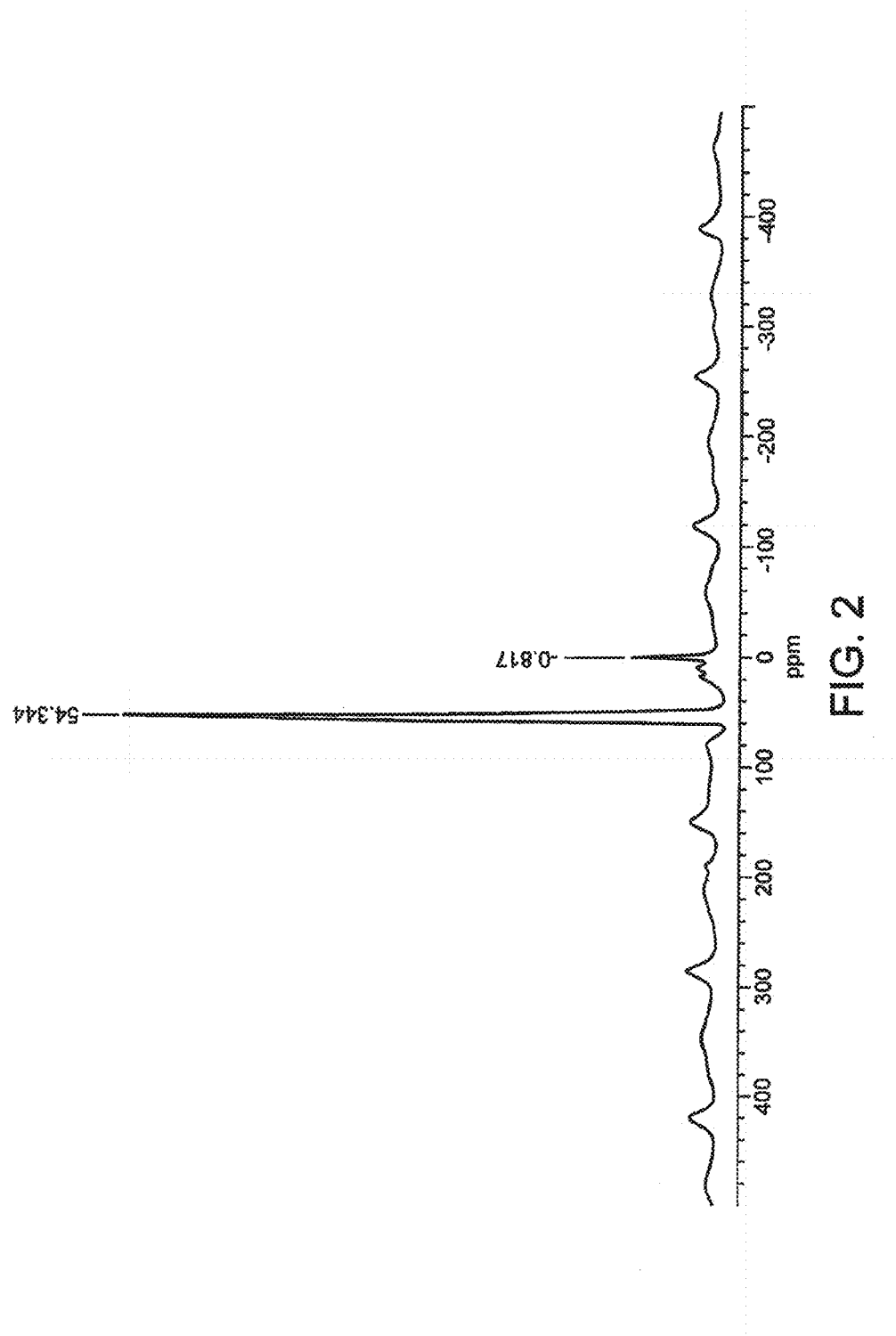

PROCESS FOR TREATING ZEOLITE CATALYSTS

This application is the U.S. national phase of International Application No. PCT/EP2014/050881 filed Jan. 17, 2014 which designated the U.S. and claims priority to European Patent Application No. 13152102.3 filed Jan. 21, 2013, the entire contents of each of which are hereby incorporated by reference.

This invention relates to a process for treating a zeolite catalyst, the catalyst so-treated and a process for the carbonylation of dimethyl ether with carbon monoxide in the presence of a treated zeolite catalyst to produce methyl acetate.

BACKGROUND OF THE INVENTION

Methyl acetate is used industrially in petrochemical processes, particularly as a feedstock for the production of commodity chemicals such as acetic acid and acetic anhydride.

Crystalline aluminosilicate zeolites have been found to catalyse the carbonylation of dimethyl ether to produce methyl acetate. For example, WO 2006/121778 describes a process for the production of a lower aliphatic ester of a lower aliphatic carboxylic acid by carbonylating lower alkyl ethers with carbon monoxide in the presence of a mordenite or ferrierite catalyst under substantially anhydrous conditions.

In U.S. Pat. No. 7,465,822 it is demonstrated that zeolites for the carbonylation of dimethyl ether to produce methyl acetate contain at least one 8-member ring channel such as those of framework type MOR, FER, OFF and GME. By contrast, zeolites not containing 8-member ring channels, such as ZSM-5 (framework type MFI), were shown to provide poor catalytic performance for this reaction.

An important aspect of any catalytic process is the performance of a catalyst when exposed to normal process conditions. The improvement of catalytic performance in carbonylation reactions is a continuous objective of process and catalyst development.

A disadvantage associated with the use of zeolites as catalysts for carbonylation processes is that they deactivate over time with a commensurate decrease in the production rate of carbonylation products. Without being bound by theory, it is believed that the deactivation of zeolite catalysts in processes for the carbonylation of dimethyl ether may be attributable to side reactions of dimethyl ether leading to the formation of hydrocarbonaceous (coke) deposits on the catalyst surface. These deposits restrict access to catalytic active sites and eventually the production rate of carbonylation products is sufficiently reduced as to necessitate replacement or regeneration of the catalyst. Processes for regenerating zeolite catalysts are disclosed for example in WO 2009/077745 and WO 2009/077739.

WO 2009/077745 describes a process for the in-situ regeneration of a mordenite catalyst in the carbonylation of a carbonylatable reactant such as dimethyl ether to form methyl acetate, in which the catalyst is regenerated by contacting the catalyst with a regenerating gas comprising a molecular oxygen-containing gas and an inert diluent at a total pressure in the range 1 to 100 bar and at an molecular oxygen-containing gas partial pressure such that the temperature of the catalyst is maintained within the range 225° C. to 325° C.

WO 2009/077739 describes a process for the in-situ regeneration of a zeolite catalyst for the production of methyl acetate by contacting a carbonylatable reactant such as dimethyl ether with carbon monoxide in the presence of the catalyst, ceasing contact of the catalyst with the carbonylatable reactant, regenerating the catalyst with a regenerating gas selected from hydrogen and a mixture of hydrogen and carbon monoxide at a temperature in the range 250 to 600° C., terminating the hydrogen regenerating step and resuming contact of the catalyst with the carbonylatable reactant and carbon monoxide.

A further disadvantage of zeolite catalysed carbonylation reactions of dimethyl ether to form methyl acetate is that the presence of water inhibits such reactions and thus typically the reactants and catalyst are dried prior to use in the carbonylation reaction.

SUMMARY OF THE INVENTION

Thus, it would be desirable to provide a process which enables zeolite catalysts to exhibit enhanced catalytic performance, such as enhanced productivity in carbonylation processes and, in particular in processes for the carbonylation of dimethyl ether to form methyl acetate.

It would also be desirable to provide zeolite catalysed processes for the carbonylation of dimethyl ether to form methyl acetate in which improved catalytic performance is achieved, and in particular in which processes an increased production rate to carbonylation reaction products is achieved.

It is understood that the formation of coke deposits is particularly prevalent during start-up of carbonylation processes, such as during start-up of processes for the carbonylation of dimethyl ether. Thus, it would also be desirable to provide a zeolite catalysed process for the carbonylation of dimethyl ether to form methyl acetate in which enhanced catalytic performance is achieved during start-up.

Applicant has now found that by pretreating a zeolite catalyst with a gas comprising at least 1 mol % water vapour and at low temperature, the catalyst exhibits improved catalytic performance in processes for the carbonylation of dimethyl ether to produce methyl acetate. In particular, catalysts so-treated allow enhanced production rates to be achieved both at start-up and throughout such carbonylation processes. Furthermore, these production rates are found to decline more slowly compared to the production rates of carbonylation processes in which untreated zeolite catalysts are utilised.

Accordingly, the present invention provides a process for treating a zeolite catalyst for the carbonylation of dimethyl ether to produce methyl acetate reaction product wherein the catalyst is contacted with a treatment gas comprising water vapour in an amount of at least 1 mol % and at a temperature below which dealumination of the zeolite structure occurs.

In some or all embodiments of the present invention, there is provided a process for treating a zeolite catalyst for the carbonylation of dimethyl ether to produce methyl acetate reaction product wherein the catalyst is contacted with a treatment gas comprising water vapour in an amount of at least 1 mol % and at a temperature below which dealumination of the zeolite structure occurs and the zeolite contains at least one channel defined by an 8-member ring.

In some or all embodiments of the present invention, the zeolite containing at least one channel defined by an 8-member ring is selected from zeolites of framework type MOR, FER, OFF and GME.

The present invention also provides a zeolite catalyst that provides improved catalytic performance for the carbonylation of dimethyl ether to produce methyl acetate reaction product wherein the catalyst is contacted with a treatment gas comprising water vapour in an amount of at least 1 mol % and at a temperature below which dealumination of the zeolite structure occurs.

In an embodiment of the present invention, the catalyst is a mordenite zeolite, preferably mordenite in the hydrogen form. In this embodiment, a mordenite may be composited with a binder, for example an inorganic oxide binder selected from aluminas, silica-aluminas and silicas. Suitably, the catalyst is mordenite composited with alumina, and preferably in the form of an extrudate.

In a further embodiment of the present invention, the treatment gas comprises water vapour in an amount of from 1 to 10 mol %, such as 3 to 6 mol % or 2 to 5 mol % and further comprises at least one of carbon monoxide, hydrogen and dimethyl ether, preferably carbon monoxide and hydrogen.

In another embodiment, the catalyst is mordenite, suitably in the hydrogen form, preferably composited with a binder selected from selected from aluminas, silica-aluminas and silicas, and the treatment gas comprises water vapour in an amount of from 1 to 10 mol %, such as 3 to 6 mol % or 2 to 5 mol % and further comprises at least one of carbon monoxide, hydrogen and dimethyl ether, preferably carbon monoxide and hydrogen.

In a yet further embodiment, the catalyst is treated during or at start-up of a process for the carbonylation of dimethyl ether to produce methyl acetate.

Without being bound by theory, it is believed that treating a zeolite catalyst in accordance with the present invention results in a more controlled accumulation and distribution of coke on the surface of the zeolite during carbonylation processes, and in particular at start-up of carbonylation processes, which mitigates catalyst deactivation and thereby allows increased production rates (space time yields) to carbonylation product to be achieved.

In addition, although carbonylation production rates inevitably decrease with time on stream, a sustained benefit in production rate has now been found to be achieved compared to corresponding carbonylation processes in which the zeolite catalyst has not been treated in accordance with the present invention.

The practical benefits of the catalysts and processes of the present invention are numerous but include benefits such as carbonylation processes may now be operated for longer durations and at improved production rates before replacement or regeneration of the catalyst is required. Due to improved catalytic performance, catalyst cost may be reduced and/or the carbonylation reactor may be reduced in size leading to a reduction in capital expenditure.

The process for treating the catalyst with the treatment gas may be carried out prior to or as part of the start-up of a carbonylation process, that is separately or in-situ within the reactor, prior to any carbonylation reaction. Preferably, treatment of the catalyst is carried out in-situ.

The catalyst is treated by contacting it with a treatment gas comprising water vapour. The amount of water vapour may be varied provided it is present in an amount of at least 1 mol %. Applicant has found that higher concentrations of water lead to higher catalytic activity. However, damage of the catalyst may arise if it is treated with water in too high a concentration. Suitably, the catalyst is contacted with a treatment gas which comprises water vapour in an amount of from 1 to 10 mol %, such as 2 to 10 mol % for example 2 to 5 mol %, and preferably in an amount of from 3 to 6 mol %.

The composition of a treatment gas may be varied. Thus, one or more gaseous components may be added to or removed from the treatment gas at any time throughout the duration of the catalyst treatment provided that water vapour is continuously maintained therein in an amount of at least 1 mol %.

The treatment gas may further comprise additional components such as at least one component selected from one or more of carbon monoxide, hydrogen, dimethyl ether.

Carbon monoxide may be substantially pure carbon monoxide as typically provided by suppliers of industrial gases, or it may contain minor quantities of other gases which do not interfere with the treatment process and the subsequent carbonylation reaction. For instance, the carbon monoxide may contain minor amounts of one or more of nitrogen, helium, argon and carbon dioxide.

Carbonylation processes of dimethyl ether with carbon monoxide can be conducted in the presence of hydrogen although in such instances the hydrogen remains largely unconsumed. However, it may be desirable to conduct a carbonylation process in this manner as it avoids the need to separate carbon monoxide and hydrogen from commercially available mixtures thereof. Commercially available mixtures of carbon monoxide and hydrogen are generally referred to in the art as synthesis gas. Conventional processes for converting hydrocarbon sources to synthesis gas include steam reforming and partial oxidation. Examples of hydrocarbon sources used in synthesis gas production include bio-mass, natural gas, methane, $C_2$-$C_5$ hydrocarbons, naphtha, coal and heavy petroleum oils.

Steam reforming generally comprises contacting a hydrocarbon with steam to form synthesis gas. The process typically includes the use of a catalyst, such as those based on nickel.

Partial oxidation generally comprises contacting a hydrocarbon with oxygen or an oxygen-containing gas such as air to form synthesis gas. Partial oxidation takes place with or without the use of a catalyst, such as those based on rhodium, platinum or palladium.

As produced, synthesis gas comprises mainly carbon monoxide and hydrogen but may also comprise minor quantities of carbon dioxide and inert gases.

Thus, the treatment gas may comprise a mixture of carbon monoxide and hydrogen, which mixture is a synthesis gas. Suitably, the treatment gas comprises a synthesis gas which has a molar ratio of carbon monoxide to hydrogen of from 15:1 to 1:3, such as from 10:1 to 1:2, and preferably from 4:1 to 1:1, such as 4:1. However, if desired other carbon monoxide:hydrogen molar ratios may also be used.

In an embodiment of the present invention, the treatment gas comprises water vapour in an amount of from 1 to 10 mol %, such as 3 to 6 mol % or 2 to 5 mol %, for example 4 to 5 mol %, and a synthesis gas. Preferably, in this embodiment the synthesis gas comprises carbon monoxide and hydrogen in a molar ratio of from 10:1 to 1:2, such as from 4:1 to 1:1, for example a molar ratio of 4:1.

If desired, hydrogen may be a component of the treatment gas in the absence of carbon monoxide.

The treatment gas may also comprise dimethyl ether, either alone or in combination with other components such as at least one of carbon monoxide and hydrogen. Suitably, dimethyl ether is present in the treatment gas at a concentration in the range of from 0.1 to 20 mol %, such as 1.5 mol % to 20 mol %, for example 1.5 mol % to 10 mol %, preferably 1.5 mol % to 5 mol % based on the total components of the treatment gas.

In an embodiment of the present invention the treatment gas comprises water vapour in an amount 1 to 10 mol %, for example 2 to 10 mol %, dimethyl ether and at least one of carbon monoxide and hydrogen, preferably a synthesis gas. Preferably, dimethyl ether is present in this embodiment at a concentration in the range of from 1.5 mol % to 10 mol %, for example 1.5 mol % to 5 mol % based on the total components of the treatment gas.

Carbon monoxide and synthesis gas are preferred components of the treatment gas, however, the treatment gas may, in addition to water vapour, include alternative or additional gaseous components. Suitably, the treatment gas may consist essentially of water vapour in an amount of at least 1 mol % and one or more of nitrogen, helium, argon and carbon dioxide. Preferably however, the treatment gas consists essentially of water vapour in an amount of at least 1 mol %, for example 2 to 10 mol % and one or more of carbon monoxide, hydrogen and dimethyl ether. More preferably, the treatment gas consists essentially of water vapour in an amount of at least 1 mol %, such as 2 to 10 mol % and a synthesis gas.

In some or all embodiments of the present invention, the treatment gas consists essentially of water vapour in an amount of 1 to 10 mol %, for example 2 to 10 mol %, such as 2 to 5 mol %, carbon monoxide and hydrogen and wherein the molar ratio of carbon monoxide to hydrogen is in the range 15:1 to 1:3, such as 10:1 to 1:2, preferably 4:1 to 1:1, for example 4:1.

The components of the treatment gas may be utilised in the form of separate streams or they may be utilised as a combined stream of one or more components.

Suitably, the catalyst is contacted with a treatment gas for a total period of from 10 minutes to 24 hours, for example from 10 minutes to 5 hours, such as from 20 minutes to 3 hours, for example from 30 minutes to 2 hours.

In some or all embodiments of the present invention, the catalyst is contacted with a treatment gas consisting essentially of water vapour in an amount of 1 to 10 mol %, for example 2 to 10 mol %, such as 2 to 5 mol %, carbon monoxide and hydrogen for a total period of from 10 minutes to 24 hours, for example from 10 minutes to 5 hours.

The catalyst is contacted with a treatment gas at a temperature below which dealumination or significant dealumination of the zeolite structure occurs. Suitably, therefore, for the purposes of the present invention, a catalyst is contacted with a treatment gas at a temperature of from 200° C. to 350° C., for instance from 230° C. to 350° C., such as from 230° C. to 320° C., for example from 250° C. to 310° C., preferably from 285° C. to 300° C.

In some or all embodiments of the present invention, the catalyst is contacted with a treatment gas consisting essentially of water vapour in an amount of 1 to 10 mol %, for example 2 to 10 mol %, such as 2 to 5 mol %, carbon monoxide and hydrogen at a temperature of from 200° C. to 350° C., for example from 250° C. to 310° C., preferably from 285° C. to 300° C. and, for example for a total period of from 10 minutes to 24 hours, such as from 10 minutes to 5 hours.

Dealumination processes are well known in the art and are used to effect the removal of aluminium from the crystalline framework of a zeolite. Conventional techniques for dealumination include hydrothermal treatments, in which dealumination of the zeolite is typically effected by processes which incorporate the use of steam in conjunction with an acidic material such as a mineral acid or an organic acid.

Removal of aluminium modifies the silica to alumina molar ratio (SAR) of the zeolite such that the SAR of the zeolite after a dealumination process is higher than that of the starting zeolite. Techniques such as X-ray fluorescence spectrometry can be used to determine the SAR of a zeolite. U.S. Pat. No. 3,551,353 describes a method for increasing the silica/alumina molar ratio of crystalline aluminosilicates having a silica/alumina molar ratio greater than 10 by a process comprising alternate steam and acid treatment of the aluminosilicate. In general, dealumination treatments are carried out at elevated temperatures such as at temperatures of 600° C. and higher.

Determination of the amount of extra-framework aluminium in a zeolite (dealumination) may be made using a number of conventional analytical techniques such as by $^{27}$Al MAS NMR.

In the present invention, treatment of the catalyst with the treatment gas is conducted at low temperatures, that is at a temperature below which any significant dealumination of the zeolite structure occurs, such that the silica:alumina molar ratio of the zeolite does not increase or substantially increase. Treatment of the catalyst causes no removal of aluminium from the zeolite framework as evidenced by $^{27}$Al MAS NMR study. Thus, a catalyst treated in accordance with the present invention retains or substantially retains its silica:alumina molar ratio.

For the purposes of the present invention, it is preferred that a treatment gas does not comprise a mineral acid such as HCl, $H_2SO_4$, $H_3PO_4$ and the like or organic acids such as carboxylic acids, for example acetic acid and dicarboxylic acids.

Suitably, the zeolite catalyst for example mordenite, may be contacted with a treatment gas comprising water vapour in an amount of at least 1 mol %, carbon monoxide and hydrogen and at a temperature of from 200° C. to 350° C. for instance from 230° C. to 350° C., such as from 230° C. to 320° C., for example from 250° C. to 310° C., preferably from 285° C. to 300° C.

In some or all embodiments of the present invention, the catalyst is a zeolite containing at least at least one channel defined by an 8-member ring, such as a zeolite of framework type MOR, FER, OFF and GME and the catalyst is contacted with a treatment gas consisting essentially of water vapour in an amount of 1 to 10 mol %, for example 2 to 10 mol %, such as 2 to 5 mol %, carbon monoxide and hydrogen at a temperature of from 200° C. to 350° C., for example from 250° C. to 310° C., preferably from 285° C. to 300° C. and, for example for a total period of from 10 minutes to 24 hours, such as from 10 minutes to 5 hours.

Suitably, the catalyst is contacted with a treatment gas at a total pressure of from 1 to 100 barg, for example 10 to 100 barg, such as 10 to 80 barg, for example 30 to 70 barg.

Desirably, the catalyst is contacted with a treatment gas at a temperature of from 230° C. to 350° C., such as 250° C. to 310° C. and at a total pressure of from 10 to 80 barg, such as 30 to 70 barg.

Suitably, the gas hourly space velocity (GHSV) of a treatment gas is in the range 500 to 40,000 $h^{-1}$, such as 2,000 to 20,000 $h^{-1}$, for example 3,000 to 10,000 $h^{-1}$.

The catalyst to be treated may comprise any crystalline zeolite which is effective to catalyse the carbonylation of dimethyl ether with carbon monoxide to produce methyl acetate.

Zeolites are commercially available in the Na-, $NH_4$-, or H-forms of the zeolite. The zeolites to be treated in the present invention are preferably in the H-form (also referred to in the art as the acid form of the zeolite). The $NH_4$-form of a zeolite can be converted to the H-form by known techniques, such as by calcining at elevated temperature, such as at temperatures of 500° C. or above, for a duration, for example of from 1 to 10 hours. The Na-form can be converted to the H-form by converting first to the $NH_4$-form by ion-exchange with an ammonium salt, such as ammonium nitrate and subsequently converting the $NH_4$-form to the H-form by calcination. Alternatively, zeolites may be synthesised using known techniques.

Zeolites comprise a system of channels which may be interconnected with other channel systems or cavities such as side-pockets or cages. The channels are defined by a series of ring structures, generally 12-member rings, 10-member rings or 8-member rings. A zeolite may contain channels of different sizes.

Suitably, the zeolites to be treated according to the present invention contain at least one channel or pocket (generically referred to throughout this specification as 'channel') which is defined by an 8-member ring. Preferably, the 8-member ring channel is interconnected with at least one channel defined by a ring with 10 or 12 members. The window size of the channel systems should be such that the reactant dimethyl ether and carbon monoxide molecules can diffuse freely in and out of the zeolite framework. Suitably, the window size of an 8-member ring channel or pocket is at least 2.5×3.6 Angstroms.

A large number of zeolite framework types are known in the art, and these are assigned three-letter structure codes by the Structure Commission of the International Zeolite Association, under the authority of IUPAC. The *Atlas of Zeolite Framework Types* (C. Baerlocher, W. M. Meier, D. H. Olson, $5^{th}$ Ed. Elsevier, Amsterdam, 2001) in conjunction with the web-based version (http://www.iza-structure.org/databases/) is a database of topological and structural details about zeolite frameworks, including the types of ring structures present in a zeolite and the dimensions of the channels defined by each ring type.

Catalysts suitable for use in the present invention are zeolites which contain at least one channel which is defined by an 8-member ring, preferably a zeolite of a framework type selected from the group consisting of MOR, for example mordenite, FER, for example ferrierite or ZSM-35, OFF, for example offretite, and GME, for example gmelinite.

In particular, the catalyst treated in accordance with the present invention is selected from mordenite, ferrierite and offretite. A preferred catalyst is mordenite and preferably mordenite in the hydrogen form.

The silica to alumina molar ratio of a catalyst to be treated in accordance with the present invention is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value. The bulk silica to alumina molar ratio of a catalyst to be treated is suitably at least 5, and preferably less than or equal to 100, such as in the range of from 7 to 40, for example in the range of from 10 to 30.

In addition to silicon and aluminium, a zeolite framework may optionally comprise trivalent framework modifier elements such as one or more of boron, gallium and iron, preferably gallium.

Where aluminium atoms in the zeolite framework have been replaced by one or more of these framework modifier elements, it is preferred that the ratio of silica to $X_2O_3$, where X is one or more trivalent elements such as one or more of aluminium, boron, gallium and iron, is at least 5 but preferably less than or equal to 100, such as in the range of from 7 to 40, for example, in the range 10 to 30.

A catalyst to be treated in accordance with the present invention may be ion-exchanged or otherwise loaded with one or more metals, such as one or more of copper, silver, nickel, iridium, rhodium, platinum, palladium and cobalt.

Zeolites are commercially available as fine crystalline powders and are typically further modified to enhance their properties for use in catalytic reactions such as by forming the zeolites into shaped particles. Processes for forming zeolites into shaped particles are well-known in the art and may be accomplished by forming a gel or paste of the zeolite powder with the addition of a suitable binder material such as a clay or an inorganic oxide, for example an inorganic oxide selected from aluminas, silica-aluminas and silicas and then extruding the gel or paste into the desired shape. Zeolite powders may also be formed into particles without the use of a binder. Typical zeolite particles include extrudates whose cross-sections are circular or embrace a plurality of arcuate lobes extending outwardly from the central portion of the zeolite particles. The zeolites to be treated in accordance with the present invention may be of any suitable shape, such as in the form of an extrudate.

In an embodiment of the present invention, the catalyst to be treated is in the form of a composite comprising a zeolite and a binder, preferably an inorganic oxide binder selected from aluminas, silica-aluminas and silicas. Preferably the zeolite is mordenite and the binder is an inorganic oxide selected from aluminas, silica-aluminas and silicas, preferably an alumina. Suitably, the composite is in the form of an extrudate.

In some or all embodiments of the present invention, a catalyst which is a mordenite in hydrogen form composited with an inorganic oxide binder such as alumina is contacted with a treatment gas consisting essentially of 2 to 10 mol % water vapour, carbon monoxide and hydrogen at a temperature from 250° C. to 310° C. such as 285° C. to 300° C. and a total pressure of from 30 to 70 barg for 10 minutes to 24 hours, for example 10 minutes to 5 hours, and suitably at a GHSV of 3,000 to 10,000 $h^{-1}$.

A catalyst treated in accordance with the present invention is particularly suitable for use in the carbonylation of dimethyl ether to produce methyl acetate.

Thus the present invention further provides a carbonylation process comprised of contacting dimethyl ether with carbon monoxide in the presence of a zeolite catalyst to produce methyl acetate reaction product, wherein the catalyst has been treated by contacting it with a treatment gas comprising water vapour in an amount of at least 1 mol % and at a temperature below which dealumination of the zeolite structure occurs.

There is further provided a process for the production of methyl acetate by the carbonylation of dimethyl ether with carbon monoxide in the presence of a treated zeolite catalyst wherein the process comprises the steps:

(i) contacting a zeolite catalyst with a treatment gas comprising water vapour in an amount of at least 1 mol % and at a temperature below which dealumination of the zeolite structure occurs; and (ii) ceasing contact of the catalyst with the water vapour; and (iii) contacting the treated catalyst with dimethyl ether and carbon monoxide to produce methyl acetate reaction product.

In the present carbonylation process, a catalyst may be contacted with a treatment gas as discussed above. The contacting of the catalyst with the treatment gas may be carried out by passing the treatment gas through a fixed bed of the catalyst.

As indicated above, dimethyl ether may be a component of the treatment gas. If desired, dimethyl ether may be present as a component of the treatment gas for the entire duration of the treatment step. However, where dimethyl ether is a component of the treatment gas, it is preferred that it is only present for a limited duration.

Suitably, dimethyl ether may be added to a treatment gas subsequent to commencing contact of the catalyst with the treatment gas comprising water vapour but prior to ceasing contact of the catalyst with water vapour. This has the benefit that a continuous supply of dimethyl ether is provided from the time of its introduction up to commencement of the carbonylation reaction and hence there is a smooth transition between the end of the treatment step and the start of the carbonylation reaction. For this mode of operation the treatment gas preferably also comprises at least one of carbon monoxide and hydrogen, for example a synthesis gas.

Thus, an embodiment of the present invention provides a process for the production of methyl acetate by the carbonylation of dimethyl ether with carbon monoxide in the presence of a treated zeolite catalyst wherein the process comprises the steps:
  (i) contacting a zeolite catalyst with a treatment gas consisting essentially of water vapour in an amount of at least 1 mol %, carbon monoxide and hydrogen at a temperature below which dealumination of the zeolite structure occurs; and
  (ii) ceasing contact of the catalyst with the water vapour; and
  (iii) contacting the treated catalyst with dimethyl ether and carbon monoxide to produce methyl acetate reaction product wherein prior to step (ii) dimethyl ether is added to the treatment gas.

Preferably, dimethyl ether is added to a treatment gas at least 1 minute prior to ceasing contact of the catalyst with water vapour, for instance at least 5 minutes prior to ceasing contact, for example at least 10 minutes prior to ceasing contact of the catalyst with water vapour.

Suitably, dimethyl ether is added to the treatment gas for 1 minute to 1 hour, such as 5 minutes to 1 hour, for example 30 minutes prior to ceasing contact of the catalyst with water vapour.

In an embodiment of the present invention the catalyst, such as a mordenite, suitably in the hydrogen form, is contacted with a treatment gas comprising water vapour in an amount of from 2 to 10 mol %, synthesis gas and dimethyl ether at a temperature of from 250° C. to 310° C., for example 285° C. to 300° C. preferably for a period of from 10 minutes to 24 hours, such as from 10 mins to 5 hours prior to ceasing contact of the catalyst with the water vapour and wherein the dimethyl ether is added to the treatment gas subsequent to commencing contact of the catalyst with the synthesis gas and water vapour components but prior to ceasing contact of the catalyst with the water vapour.

In a variant, contact of the catalyst with water vapour may be ceased on or after detection of dimethyl ether in the effluent stream from a catalyst treatment. In this mode of operation, dimethyl ether is added to a treatment gas, preferably a treatment gas comprising a synthesis gas, subsequent to commencing the treatment step, an effluent stream is withdrawn from the treatment step and whereupon, or subsequent to, dimethyl ether is detectable in the effluent stream, contact of the catalyst with water vapour is ceased. Suitably dimethyl ether is added to the treatment gas subsequent to commencing the treatment step and is continuously added thereto at least until dimethyl ether is detectable in the effluent stream from the treatment step whereupon, or subsequent to, contact of the catalyst with water vapour is ceased. The presence of dimethyl ether in an effluent stream from the treatment step may be detected using any suitable analytical technique, for example by gas chromatography.

After the desired duration of exposure of the catalyst to the treatment gas, the contact of the catalyst with water vapour is ceased.

After ceasing contact of the catalyst with water vapour, the treated catalyst is contacted with dimethyl ether and carbon monoxide to produce methyl acetate reaction product. Preferably, the steps of ceasing contact of the catalyst with water vapour and contacting the catalyst with carbon monoxide and dimethyl ether are carried out concurrently or in immediate succession, that is substantially without interruption.

Where dimethyl ether is a component of a treatment gas which also comprises carbon monoxide, the carbonylation reaction to produce methyl acetate reaction product is initiated on ceasing contact of the catalyst with the water vapour.

Where dimethyl ether is not a component of the treatment gas, the carbonylation reaction to produce methyl acetate reaction product may be initiated by commencing contact of the treated catalyst with dimethyl ether (and carbon monoxide if not present in the treatment gas) on or after ceasing contact of the catalyst with the water vapour. Suitably, the treated catalyst is contacted with dimethyl ether (and carbon monoxide, if not present in the treatment gas) no more than 30 seconds, preferably no more than 10 seconds, such as no more than 5 seconds, for example no more than 1 second after ceasing contact of the catalyst with water vapour.

Once contact of the catalyst with water vapour is ceased and the treated catalyst is contacted with dimethyl ether and carbon monoxide, the carbonylation reaction to produce methyl acetate reaction product will be initiated. Any suitable carbonylation reaction conditions, such as those made with reference to step (iii) below, may be employed in the carbonylation reaction step of the processes of the present invention Suitably, in step (iii) the concentration of dimethyl ether is in the range of from 0.1 to 20 mol %, such as 1 mol % to 20 mol %, preferably 2 mol % to 15 mol %, for example 4 mol % to 12 mol % based on the total gaseous feed to the carbonylation reaction.

The molar ratio of carbon monoxide to dimethyl ether in step (iii) is suitably in the range of from 1:1 to 99:1, such as from 2:1 to 60:1.

Suitably, the partial pressure of carbon monoxide in step (iii) is in the range of from 1 to 60 barg, such as 10 to 50 barg, for example 20 to 50 barg.

Step (iii) may be conducted in the presence of hydrogen. The hydrogen may be supplied to the carbonylation reaction as a combined stream with at least one of carbon monoxide and dimethyl ether or may be supplied as a separate stream.

Suitably, in step (iii) a synthesis gas may be used as the source of carbon monoxide. Suitably, the synthesis gas has a molar ratio of carbon monoxide to hydrogen of from 15:1 to 1:3, for example from 10:1 to 1:2, and preferably from 4:1 to 1:1. However, if desired other carbon monoxide:hydrogen molar ratios may also be used.

Step (iii) is suitably conducted at a temperature of from 240 to 350° C., such as from 250 to 350° C., for example from 275 to 350° C., and preferably from 275 to 325° C.

Step (iii) is suitably carried out at a total pressure in the range 1 to 100 barg, for example 10 to 100 barg, such as 20 to 90 barg, for example 40 to 80 barg, or 50 to 80 barg.

Desirably, step (iii) is conducted at a temperature in the range of from 250° C. to 350° C., for example from 275° C. to 350° C. and at a total pressure in the range of from 10 to 100 barg, such as 40 to 80 barg.

As water inhibits the carbonylation of dimethyl ether to form methyl acetate, step (iii) is preferably conducted under substantially anhydrous conditions. As used herein, "substantially anhydrous conditions" is taken to mean that the amount of water fed to the carbonylation reaction is less than 1 mol %, preferably less than 0.5 mol %, more preferably less than 0.2 mol %, and most preferably less than 0.1 mol % based on the total gaseous feed to the carbonylation reaction.

Step (iii) is suitably carried out at a gas hourly space velocity (GHSV) in the range of from 500 to 40,000 $h^{-1}$, such as 2,000 to 20,000 $h^{-1}$, for example 3,000 to 10,000 $h^{-1}$.

Step (iii) is generally carried out as a vapour phase process, for example, as a fixed bed or fluidised bed process.

Where the carbonylation reaction is operated as a vapour phase process, the reactants, prior to being fed into the reactor, may be in the liquid phase. However, prior to contact with the treated catalyst, liquid phase components should be volatilised, for example by use of a pre-heater.

Step (iii) may be carried out by passing a gaseous feed of dimethyl ether and carbon monoxide and optionally hydrogen, through a fixed bed or fluidised bed of the treated catalyst maintained at the desired reaction temperature. Preferably, the carbonylation is carried out by passing a gaseous feed of dimethyl ether and synthesis gas through a fixed bed of the treated catalyst maintained at the desired reaction temperature.

The reaction product of step (iii) comprises methyl acetate. Typically the reaction product may further comprise additional components such as one or more of unreacted dimethyl ether, unreacted carbon monoxide and hydrogen.

Desirably, methyl acetate is recovered from the reaction product and some or all of the recovered methyl acetate is converted to acetic acid.

The reaction product is typically in gaseous form. Suitably, the reaction product is cooled and separated to recover a methyl acetate-rich liquid stream and a gas stream comprising for example unreacted carbon monoxide and hydrogen. Cooling of the reaction product may be carried out using one or more heat exchange means, such as conventional heat exchangers, to cool the reaction product to, for example a temperature of 50° C. or less. A methyl acetate-rich liquid stream may be recovered from the gas stream, for example in one or more gas/liquid separation means such as a knock-out drum or a tangential inlet drum.

The methyl acetate-rich liquid stream comprises mainly methyl acetate and may also comprise minor amounts of one or more of unreacted dimethyl ether, water and dissolved inert gases. Methyl acetate may be recovered from the methyl acetate-rich liquid stream, for example by distillation, and sold as such or used as a feedstock in downstream chemical processes. Suitably some or all of the recovered methyl acetate may be converted to acetic acid, preferably by a hydrolysis process. Hydrolysis of the recovered methyl acetate may be carried out using known processes, such as catalytic distillation processes. Typically, in catalytic distillation processes for the hydrolysis of methyl acetate, methyl acetate is hydrolysed with water in a fixed-bed reactor employing an acidic catalyst, such as an acidic ion exchange resin or a zeolite, to produce a mixture comprising acetic acid and methanol from which acetic acid and methanol may be separated by distillation, in one or more distillation stages.

The present invention will now be illustrated with reference to the following non-limiting examples.

Catalyst

The catalyst employed in each of the examples was H-mordenite (SAR 20) composited with 20 wt % alumina in the form of 1.6 mm extrudates (ex Zeolyst International Inc. Lot number 2518-151-1).

Apparatus

Each of the examples was conducted in a plug-flow reactor tube having an internal diameter of 24 mm and capable of operation at temperatures of up to 350° C. and at pressures of up to 80 barg. The reactor tube was mounted vertically and packed with an inert supporting bed of 12.5 mL silicon carbide, a catalyst bed of 50 mL of catalyst diluted with 120 mL silicon carbide and an inert top layer of 40 mL silicon carbide. The reactor was equipped with independent gas feeds for synthesis gas and nitrogen controlled by independent mass-flow controllers and two independent liquid feeds to an in-line vaporiser for the supply of water vapour and gaseous dimethyl ether. The exit stream from the reactor was passed periodically to two gas chromatographs (GC) for analysis. A first GC was a Chrompack CP-2002 gas chromatograph fitted with a TCD detector equipped with a Molsieve 5A (15 m*0.32 mm) column. The second GC was a Chrompack CP-9003 equipped with a TCD and FID detector. The stream to the second GC was split into two with one stream passing through a PoraPlot Q (30 m*0.32 mm column and the second stream passing through a PoraPlot Q (30 m*0.53 mm pre-separation column followed by a Molsieve 5A (15 m*0.32 mm) column The space time yields (STY), calculated as acetic acid equivalents per $dm^3$ of catalyst per hour, were determined at periodic intervals. Acetic acid equivalents were determined by multiplying the STY for methyl acetate production by 0.81 [i.e. molecular weight (acetic acid)/molecular weight (methyl acetate)].

BRIEF DESCRIPTION OF THE DRAWINGS

The invention is further described with reference to the accompanying drawings, in which:

FIG. 1 shows the $^{27}$Al NMR spectrum for the untreated catalyst:

FIG. 2 shows the $^{27}$Al NMR spectrum for the treated catalyst.

EXAMPLES

Example 1

Not in Accordance with the Invention

This example employed the catalyst and apparatus as described above and demonstrates the carbonylation of dimethyl ether in the presence of a catalyst which has not been pretreated with water vapour.

Synthesis gas having a carbon monoxide to hydrogen molar ratio of 4:1 was fed into the reactor which was heated to 285° C. at a pressure of 70 barg and a gas hourly space velocity (GHSV) of 5000 $h^{-1}$ and contacted the catalyst.

After 16 hours dimethyl ether was added to the synthesis gas at a concentration of 5 mol % relative to the total amount of synthesis gas and dimethyl ether. After a further 10 hours the dimethyl ether concentration was increased to 10 mol %. After 40 hours the temperature of the reactor was increased from 285° C. to 300° C. and maintained at this temperature for a further 60 hours. The space time yields (STY) obtained after 40, 45 and 100 hours on stream are given in Table 1 below.

Example 2

This example used the catalyst and apparatus as described above and demonstrates the carbonylation of dimethyl ether in the presence of a catalyst pretreated with synthesis gas comprising 5 mol % water vapour.

Synthesis gas having a carbon monoxide to hydrogen molar ratio of 4:1 and comprising 5 mol % water vapour was fed into the reactor which was heated to a temperature of 285° C. at a pressure of 70 barg and at a GHSV of 5000 h$^{-1}$. The water-containing synthesis gas contacted the catalyst for 5 hours after which time the supply of water vapour was ceased and dimethyl ether was immediately introduced into the reactor at a concentration of 5 mol % relative to the total amount of dimethyl ether and synthesis gas. After a further 10 hours the concentration of dimethyl ether was increased to 10 mol %. After 40 hours the temperature was increased from 285° C. to 300° C. and maintained at this temperature for a further 60 hours. The space time yields (STY) after 40, 45 and 100 hours on stream are given in Table 1 below.

TABLE 1

| Time on stream (hours) | Temp. (° C.) | STY (g/dm$^3$/h) Ex. 1 (untreated) | Ex. 2 | % STY increase |
| --- | --- | --- | --- | --- |
| 40 | 285 | 225 | 410 | 82 |
| 45 | 300 | 420 | 790 | 88 |
| 100 | 300 | 355 | 585 | 65 |

From an inspection of Table 1 it can clearly be seen that by treating the catalyst with water vapour prior to its use in the carbonylation reaction a material improvement in production rate is achieved.

Example 3

Example 2 was repeated using synthesis gas containing 2 mol % water vapour.

A comparison of the results of Example 1 (untreated catalyst) and Example 3 are given in Table 2 below.

TABLE 2

| Time on stream (hours) | Temp. (° C.) | STY (g/dm$^3$/h) Ex. 1 (untreated catalyst) | Ex. 3 | % STY increase |
| --- | --- | --- | --- | --- |
| 40 | 285 | 225 | 280 | 24 |
| 45 | 300 | 420 | 560 | 33 |
| 100 | 300 | 355 | 430 | 21 |

Example 4

Example 2 was repeated using synthesis gas containing 10 mol % water vapour and a carbonylation reaction time of 200 hours after which time the reaction was terminated.

A comparison of the results of Example 1 (untreated catalyst) and Example 4 are given in Table 3 below.

TABLE 3

| Time on stream (hours) | Ex. 1 (untreated catalyst) Temp. (° C.) | STY (g/dm$^3$/h) | Ex. 4 Temp. (° C.) | STY (g/dm$^3$/h) |
| --- | --- | --- | --- | --- |
| 40 | 285 | 225 | 285 | 280 |
| 45 | 300 | 420 | 285 | 285 |
| 100 | 300 | 355 | 285 | 345 |
| 180 | 300 | 320 | 285 | 360 |
| 200 | n/a | n/a | 300 | 610 |
| 250 | n/a | n/a | 300 | 600 |

Example 5

This example employed the catalyst and apparatus as described above. Synthesis gas having a carbon monoxide to hydrogen molar ratio of 4:1 and comprising water vapour at a concentration of 4 mol % was fed to the reactor which was heated to 285° C., at a pressure of 70 barg and a GHSV of 5000 h$^{-1}$. The water-containing synthesis gas contacted the catalyst for a period of 5 hours at which time dimethyl ether was introduced into the reactor at a concentration of 5 mol % relative to the total amount of dimethyl ether, synthesis gas and water. On detection of dimethyl ether in the effluent stream exiting the reactor, the supply of water vapour to the reactor was ceased. After 10 hours on stream the concentration of dimethyl ether was increased to 10 mol % and the experiment was run for a further 100 hours. The STY results of Example 5 are summarised in Table 4 below.

TABLE 4

| Time on stream (hours) | Temp. (° C.) | STY (g/dm$^3$/h) |
| --- | --- | --- |
| 40 | 285 | 490 |
| 100 | 285 | 480 |

Example 6

This example employed the catalyst and apparatus as described above. The catalyst was treated with synthesis gas comprising 5 mol % water vapour as follows. Synthesis gas having a carbon monoxide to hydrogen molar ratio of 4:1 and comprising 5 mol % water vapour was supplied to the reactor which was heated to 285° C. at a pressure of 70 barg and a GHSV of 5000 h-1 and the water-containing synthesis gas contacted for 8 hours. After 8 hours the supply of water vapour was ceased and the catalyst was discharged from the reactor after purging it with nitrogen and allowing the reactor to cool down.

A sample of the treated catalyst (treated sample) and a sample of the catalyst prior to treatment (untreated sample) were analysed by $^{27}$Al NMR spectroscopy to determine whether the treatment of the catalyst with the water vapour had caused dealumination of the zeolite structure. The $^{27}$Al NMR spectra were obtained using a Varian Unity VNMRS spectrometer operating at 104.20 MHz. A 4 mm (rotor o.d.) magic-angle spinning (MAS) probe. $^{27}$Al spectra were acquired using a direct-polarisation (DP) experiment with sample spin-rates of approximately 14 kHz. Spectral referencing was with respect to 1M aqueous AlCl$_3$. Spectra were recorded from 50 mg of each of the treated and untreated samples which had been hydrated with water (100 microliters) and then dried.

As the untreated and treated samples were extrudates containing alumina as the binder a modified NMR technique was used to obtain spectra from which the amount of extra framework aluminium in a sample could be measured. The technique made use of the fact that aluminium atoms in the alumina binder and in the mordenite have different quadrupolar couplings. As the effect of the RF pulse in NMR spectroscopy is proportional to the quadrupolar coupling of the species being observed a pulse duration (4.2 microseconds) was found which resulted in little excitation to the aluminium atoms in the alumina binder but still resulted in a reasonable signal for the aluminium atoms in the mordenite. Deconvolution of the peak at ca. 0.8 ppm in the $^{27}$Al NMR spectrum was then used to estimate the intensity of any residual signal (at ca. 7 ppm) from the alumina binder to allow the amount of extra framework aluminium to be calculated. The $^{27}$Al NMR spectra for the untreated and treated catalyst are shown in FIG. 1 and FIG. 2 respectively.

The % of extra framework aluminium was found to be 11.±1% in the untreated sample and 12±1% in the treated sample. The amount of extra framework aluminium had not increased significantly with the conclusion that dealumination of the zeolite had not occurred to any significant extent.

Example 7

This example employed the catalyst and apparatus as described above. Synthesis gas having a carbon monoxide to hydrogen molar ratio of 4:1 and comprising water vapour at a concentration of 5 mol % was fed to the reactor which was heated to 270° C., at a pressure of 70 barg and a GHSV of 5000 h$^{-1}$. The water-containing synthesis gas contacted the catalyst for a period of 5 hours and 30 minutes. For the last 30 minutes dimethyl ether was introduced into the reactor at a concentration of 5 mol % relative to the total amount of dimethyl ether, synthesis gas and water. 30 minutes after the feed of dimethyl ether was started, the supply of water vapour to the reactor was ceased. 10 hours after the water vapour was ceased, the concentration of dimethyl ether was increased to 10 mol % and after a further 8 hours the temperature was gradually increased to 290° C. The results are summarised in Table 5 below.

TABLE 5

| Time on stream (hours) | Temp. (° C.) | STY (g/dm$^3$/h) |
|---|---|---|
| 40 | 275 | 257 |
| 91 | 285 | 449 |
| 114 | 290 | 522 |

The invention claimed is:

1. A process for treating a zeolite catalyst for the carbonylation of dimethyl ether to produce methyl acetate wherein the catalyst is contacted with a treatment gas comprising water vapour in an amount of at least 1 mol % and at a temperature below which dealumination of the zeolite structure occurs and wherein the zeolite contains at least one channel which is defined by an 8-member ring and is mordenite.

2. A carbonylation process comprised of contacting dimethyl ether with carbon monoxide in the presence of a zeolite catalyst to produce methyl acetate reaction product, wherein the catalyst has been treated by contacting it with a treatment gas comprising water vapour in an amount of at least 1 mol % and at a temperature below which dealumination of the zeolite structure occurs and wherein the zeolite contains at least one channel which is defined by an 8-member ring and is mordenite.

3. A process for the production of methyl acetate by the carbonylation of dimethyl ether with carbon monoxide in the presence of a treated zeolite catalyst wherein the process comprises the steps (i) contacting a zeolite catalyst with a treatment gas comprising water vapour in an amount of at least 1 mol % and at a temperature below which dealumination of the zeolite structure occurs and wherein the zeolite contains at least one channel which is defined by an 8-member ring and is mordenite; and (ii) ceasing contact of the catalyst with the water vapour; and (iii) contacting the treated catalyst with dimethyl ether and carbon monoxide to produce methyl acetate reaction product.

4. A process according to claim 1 wherein the mordenite is in the hydrogen form.

5. A process according to claim 1 wherein the zeolite in addition to silicon and aluminium comprises a trivalent framework modifier element selected from one or more of boron, gallium and iron.

6. A process according to claim 1 wherein the catalyst is in the form of a composite comprising the zeolite and an inorganic oxide binder selected from aluminas, silica-aluminas and silicas.

7. A process according to claim 1 wherein the catalyst is contacted with the treatment gas at a temperature of from 200° C. to 350° C.

8. A process according to claim 7 wherein the temperature is from 250 C to 310° C.

9. A process according to claim 8 wherein the temperature is from 285° C. to 300° C.

10. A process according to claim 1 wherein the treatment gas comprises from 1 to 10 mol % water vapour.

11. A process according to claim 10 wherein the treatment gas comprises from 2 to 10 mol % water vapour.

12. A process according to claim 1 wherein the treatment gas further comprises at least one component selected from one or more of carbon monoxide, hydrogen and dimethyl ether.

13. A process according to claim 1 wherein the treatment gas further comprises synthesis gas.

14. A process according to claim 13 wherein the synthesis gas has a molar ratio of carbon monoxide to hydrogen of from 15:1 to 1:3.

15. A process according to claim 14 wherein the molar ratio is 4:1 to 1:1.

16. A process according to claim 1 wherein the catalyst is contacted with the treatment gas for a period of from 10 minutes to 24 hours.

17. A process according to claim 1 wherein the catalyst is contacted with the treatment gas at a pressure in the range of from 10 to 100 barg.

18. A process according to claim 1 wherein the catalyst is contacted with the treatment gas at a gas hourly space velocity in the range 3000 to 10,000 h$^{-1}$.

19. A process according to claim 3 wherein dimethyl ether is added to a treatment gas subsequent to commencing contact of the catalyst with the treatment gas but prior to ceasing contact of the catalyst with the water vapour.

20. A process according to claim 19 wherein dimethyl ether is added to the treatment gas for up to 1 minute to 1 hour prior to ceasing contact of the catalyst with water vapour.

21. A process according to claim 19 wherein dimethyl ether is added to the treatment gas at a concentration in the range 0.1 to 20 mol % based on the total components of the treatment gas.

22. A process according to claim 21 wherein the dimethyl concentration is in the range 1.5 to 5 mol % based on the total components of the treatment gas.

23. A process according to claim 3 wherein in step (iii) a synthesis gas is employed as the source of carbon monoxide.

24. A process according to claim 3 wherein step (iii) is carried out at a temperature of from 250° C. to 350° C. and at a total pressure of from 10 to 100 barg.

25. A process according to claim 3 wherein methyl acetate is recovered from the reaction product and some or all of the recovered methyl acetate is converted to acetic acid.

* * * * *